(12) United States Patent
Florent et al.

(10) Patent No.: US 8,255,037 B2
(45) Date of Patent: Aug. 28, 2012

(54) CARDIAC ROADMAPPING

(75) Inventors: Raoul Florent, Ville d'Avray (FR); Stephane Valente, Paris (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 321 days.

(21) Appl. No.: 12/529,349

(22) PCT Filed: Feb. 25, 2008

(86) PCT No.: PCT/IB2008/050667
§ 371 (c)(1),
(2), (4) Date: Oct. 28, 2009

(87) PCT Pub. No.: WO2008/107814
PCT Pub. Date: Sep. 12, 2008

(65) Prior Publication Data
US 2010/0049038 A1    Feb. 25, 2010

(30) Foreign Application Priority Data
Mar. 2, 2007  (EP) ..................... 07103434

(51) Int. Cl.
*A61B 5/05* (2006.01)
(52) U.S. Cl. ...................................... 600/425
(58) Field of Classification Search ............. 600/425
See application file for complete search history.

(56) References Cited

U.S. PATENT DOCUMENTS

| 6,711,433 B1 | 3/2004 | Geiger et al. |
| 2005/0027193 A1 | 2/2005 | Mitschke et al. |
| 2006/0257006 A1 * | 11/2006 | Bredno et al. ............... 382/128 |
| 2007/0167721 A1 | 7/2007 | Pfister et al. |
| 2010/0302383 A1 * | 12/2010 | Fuh et al. ................. 348/208.4 |

FOREIGN PATENT DOCUMENTS

| WO | 2004034329 A2 | 4/2004 |
| WO | 2005039253 A1 | 4/2005 |
| WO | 2005070318 A1 | 8/2005 |

OTHER PUBLICATIONS

Bredno et al: "Algorithmic Solutions for Live Device-to-Vessel Match"; Medical Imaging 2004:Image Processing, J. Michael Fitzpatrick, Milan Sonka (Eds), Proceedings of SPIE, Vol. 5370, May 2004, pp. 1486-1497.
Krueger et al: Modality-Integrated Magnetic Catheter Tracking for X-Ray Vascular Interventions; Physics in Medicine and Biology, vol. 50, 2005, pp. 581-597.
Schafer et al: "Three-Dimensional Reconstruction of Coronary Stents in Vivo Based on Motion Compensated X-Ray Angiography"; Medical Imaging 2007: Visualization and Image-Guided Procedures, Kevin R. Cleary, Michael I. Miga (Eds), Proceedings of SPIE, vol. 6509, 2007, pp. 65091M-65091M-8.
Timinger et al: "Motion Compensation for Interventional Navigation on 3D Static Roadmaps Based on an Affine Model and Gating"; Physics in Medicine and Biology, Vol. 49 (2004), pp. 719-732.

* cited by examiner

*Primary Examiner* — Brian Casler
*Assistant Examiner* — Saurel J Selkin

(57) ABSTRACT

According to an exemplary embodiment of the present invention, a cardiac roadmapping technique is provided, in which a static roadmap is built onto which a view of the intervention device is projected at the correct location. This new viewing mode combines the advantages of both roadmapping, i.e. accurate localization, and the advantages of a motion-free view, i.e. maximum readability.

14 Claims, 3 Drawing Sheets

CARDIAC ROADMAPPING

The invention relates to the field of interventional imaging. In particular, the invention relates to an examination apparatus for cardiac roadmapping for examination of an object of interest located in a volume of interest, to a method for cardiac roadmapping, a computer-readable medium, a program element and an image processing device.

For treating cardiac stenoses, an imaging system for percutaneous transluminal coronary angioplasty (PTCA) may be used in catheter laboratories. In the following, a basic interventional procedure is described, which can be found in [3]:

"After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms ( . . . ). During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire ( . . . ) and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled."

In [3], an overlay technique between the angiogram and the live images (referred to as roadmapping) is described:

"In such procedures, the vessel structure itself is not visible during the intervention as it is not radio-opaque. Consequently, the navigation and precise positioning of guidewire and interventional devices is tedious, time-consuming, and requires additional contrast agent bursts to clarify the position of the devices relative to the relevant vessels. Due to scatter, both patient and medical staff are exposed to x-ray during the acquisition of diagnostic angiograms and interventional fluoroscopy. Consequently, navigation support is desired to reduce the intervention time and to enhance the positioning accuracy. Routinely, a static diagnostic angiogram acquired with a similar imager geometry is displayed next to the live interventional fluoroscopy. For the navigation of guidewire and devices within the vessels, a subjective visual fusion of the static angiogram and the live fluoroscopy is required. An improved context-rich visualization could give important support in navigation. As a straightforward approach, preprocessed angiograms can be overlaid onto the fluoroscopic image stream so that vessels and the interventional devices are synchronously displayed on one screen. However, between the acquisition of diagnostic angiograms and the fluoroscopy, time has passed and unintended as well as deliberate patient movements result in changes of position and orientation as well as soft tissue deformation. For coronary interventions, also the vessel structure continuously changes due to heart beat and respiration movement. Consequently, such overlay techniques suffer from mismatches of interventional fluoroscopy and diagnostic overlay ( . . . ). As a result, guidewire and interventional devices are not displayed inside a vessel, the perceived quality of the overlay images is poor."

A navigation may therefore help the cardiologist by providing a cardiac roadmap displayed next or overlaid on the life fluoroscopy pictures. Ideally, this cardiac roadmap represents the vessel network acquired during angiography, with the same cardiac phase than the current life image.

Documents [1] and [2] describe a basic method for realizing cardiac roadmapping. They rely on the extraction of the cardiac and respiratory cycles, and on the matching of those cycles between the angiogram images (in filled state) and the life images.

Roadmapping is a very important feature since it may provide the accurate localization of the intervention device with respect to the vessel anatomy, which would otherwise be invisible during most of the PTCA time.

Roadmapping is even more interesting in the case of cardiac interventions since the mental registration otherwise performed by the cardiologist between the angiogram (usually one selected image) and the dynamic fluoroscopy sequence is a tiring and inaccurate process.

However, no matter how good cardiac roadmapping may be, the overlay result may remain a dynamic view that incorporates both the cardiac and breathing motions, and even possible patient motion. The superimposition of those motions may be an extra factor of fatigue. In addition, imperfection of the roadmapping process may tend to create some small jitters between the intervention objects and the roadmapping indications, thus adding to the complexity of the dynamic roadmapping view.

It may be desirable to provide for an improved motion-free interventional cardiac roadmapping.

The invention provides an examination apparatus for cardiac roadmapping for examination of an object of interest located in a volume of interest, an image processing device, a computer-readable medium, a program element and a method of examining an object of interest with the features according to the independent claims.

It should be noted that the following described exemplary embodiments of the invention apply also for the method of examination of the object of interest, for the computer-readable medium, for the image processing device and for the program element.

According to a first aspect of the present invention, an examination apparatus for cardiac roadmapping for examination of an object of interest located in a volume of interest is provided, the examination apparatus comprising a calculation unit adapted for performing a reference map creation of the volume of interest on the basis of a first image sequence of the volume of interest, a device map sequence creation of the volume of interest on the basis of a second image sequence of the volume of interest, and a projection of the device map sequence onto the reference map, resulting in a navigation sequence, wherein the reference map is a static roadmap of the object of interest.

In other words, a device map sequence which may be acquired during an intervention is overlaid onto a static, frozen reference map depicting the same area (i.e. the volume of interest). This may overcome the visualization problems created by the various motion during cardiac roadmapping display, such as breathing, heart beating, patient motion, or roadmap-to-reality jitter. Furthermore, this may provide a motion-free visual support for maximum readability.

According to another exemplary embodiment of the present invention, the object of interest is a cardiac vessel-tree, wherein the first image sequence is an angiogram of the object of interest, wherein the second image sequence is a life-time sequence acquired during an intervention of the object of interest, and wherein the reference map is a reference vessel-map.

Therefore, the reference map is a static reference map and the first image sequence refers to an angiographic sequence.

A plurality of device maps are created, for example one device map per fluoroscopic image (i.e. the second image sequence is a fluoroscopic sequence). It should be noted however, that for each built device map, several fluoro image may be involved, i.e. there does not have to be a one-to-one correspondence between device maps and fluoro images.

According to another exemplary embodiment of the present invention, the projection of the device map onto the reference map is a registration performed on the basis of a sequence of composed motion vector fields, resulting in a sequence of registered device maps.

According to another exemplary embodiment of the present invention, the reference vessel map is selected from a vessel map sequence.

Furthermore, according to another exemplary embodiment of the present invention, the selection of the reference vessel map comprises a vessel cycle extraction corresponding to a full cardiac cycle.

According to another exemplary embodiment of the present invention, the calculation unit is further adapted for performing a device map to vessel map motion estimation after creation of the device map, resulting in a first sequence of motion vector fields.

Furthermore, according to another exemplary embodiment of the present invention, the device map to vessel map motion estimation comprises a sequence-to-sequence motion estimation and matching operation.

Thus, the motion estimation step may take into account spatial-temporal constraints (as opposed to an image-to-image or even to an image-to-sequence process).

According to another exemplary embodiment of the present invention, the calculation unit is further adapted for performing a vessel map to reference map motion estimation after creation of the reference map, resulting in a second sequence of vector fields. Furthermore, the calculation unit is adapted for performing a motion composition on the basis of the first and second sequences of vector fields, resulting in the sequence of composed motion vector fields.

According to a further exemplary embodiment of the present invention, the calculation unit is adapted for superimposing the sequence of registered device maps to the reference vessel map.

This may produce the final results, which are depicted in FIG. 3.

The examination apparatus may be configured as one of the group consisting of a material testing apparatus, a medical application apparatus and a micro CT system.

A field of application of the invention may be medial imaging, such as cardiac imaging, or baggage inspection.

According to another exemplary embodiment of the present invention, the examination apparatus is adapted as one of a three-dimensional computed tomography apparatus at a three-dimensional rotational X-ray apparatus.

Furthermore, according to another exemplary embodiment of the present invention, a method for cardiac roadmapping for examination of an object of interest located in a volume of interest with an examination apparatus is provided, in which a reference map of the volume of interest is created on the basis of a first image sequence of the volume of interest, a device map of the volume of interest is created on the basis of a second image sequence of the volume of interest, and in which a projection of the device map onto the reference map is performed, wherein the reference map is a static roadmap of the object of interest.

According to another exemplary embodiment of the present invention, an image processing device for cardiac roadmapping for examination of an object of interest located in a volume of interest is provided, the image processing device comprising a memory for storing a data set of the object of interest, wherein the image processing device is adapted for carrying out the above-mentioned method steps, e.g. by means of a calculation unit.

According to another exemplary embodiment of the present invention, a computer-readable medium is provided, in which a computer program for cardiac roadmapping is stored which, when being executed by a processor, causes the processor to carry out the above-mentioned method steps.

Furthermore, according to another exemplary embodiment of the present invention, a program element for cardiac roadmapping for examination of an object of interest is provided which, when being executed by a processor, causes the processor to carry out the above-mentioned method steps.

Those skilled in the art will readily appreciate that the method of examination of the object of interest may be embodied as the computer program, i.e. by software, or may be embodied using one or more special electronic optimization circuits, i.e. in hardware, or the method may be embodied in hybrid form, i.e. by means of software components and hardware components.

The program element according to an exemplary embodiment of the invention may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that a static roadmap is created on which a (possibly stylised) view of the invention device is projected at the correct location. This purely synthetic view may provide both the roadmapping information (that is the accurate localization of the intervention device with respect to the vessel anatomy), and a high degree of readability offered both by the stillness of the view and by its synthetic character.

These and other aspects of the present invention will become apparent from and elucidated with reference to the embodiments described hereinafter.

It should be noted that the invention is not limited to a specific implementation. Rather, the general notion of "cardiac roadmapping and freezing" characterizes a gist of the invention.

Exemplary embodiments of the present invention will now be described in the following, with reference to the following drawings.

The illustration in the drawings is schematic. In different drawings, similar or identical elements are provided with the same reference numerals.

Figure 1:
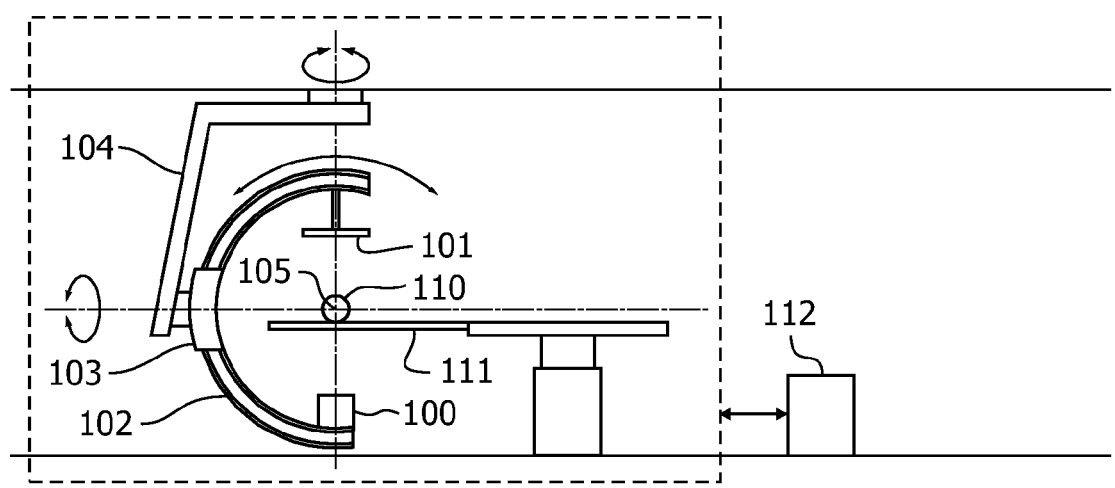
FIG. 1 shows a simplified schematic representation of a C-arm rotational X-ray examination apparatus according to an exemplary embodiment of the present invention.

FIG. 1 shows a schematic representation of an exemplary rotational X-ray scanner in which a method according to the invention may be implemented. An X-ray source 100 and a flat detector 101 with a large sensitive area are mounted to the ends of a C-arm 102. The C-arm 102 is held by curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are effected by servo motors. The axes of the three rotational movements and the cone-beam axis always meet in a single fixed point, the "isocenter" 105 of the rotational X-ray scanner. There is a certain volume around the isocenter that is projected by all cone beams along the source trajectory. The shape and size of this "volume of projection" (VOP) depend on the shape and size of the detector and on the source trajectory. In FIG. 1, the ball 110 indicates the biggest isocentric ball that fits into the VOP. The object (e.g. a patient or an item of baggage) to be imaged is placed on the table 111 such that the object's volume of interest (VOI) fills the VOP. If the object is small enough, it will fit completely into the VOP; otherwise, not. The VOP therefore limits the size of the VOI.

The various rotational movements are controlled by a control unit 112. Each triple of C-arm angle, sleeve angle, and L-arm angle defines a position of the X-ray source. By varying these angles with time, the source can be made to move along a prescribed source trajectory. The detector at the other end of the C-arm makes a corresponding movement.

Figure 2:
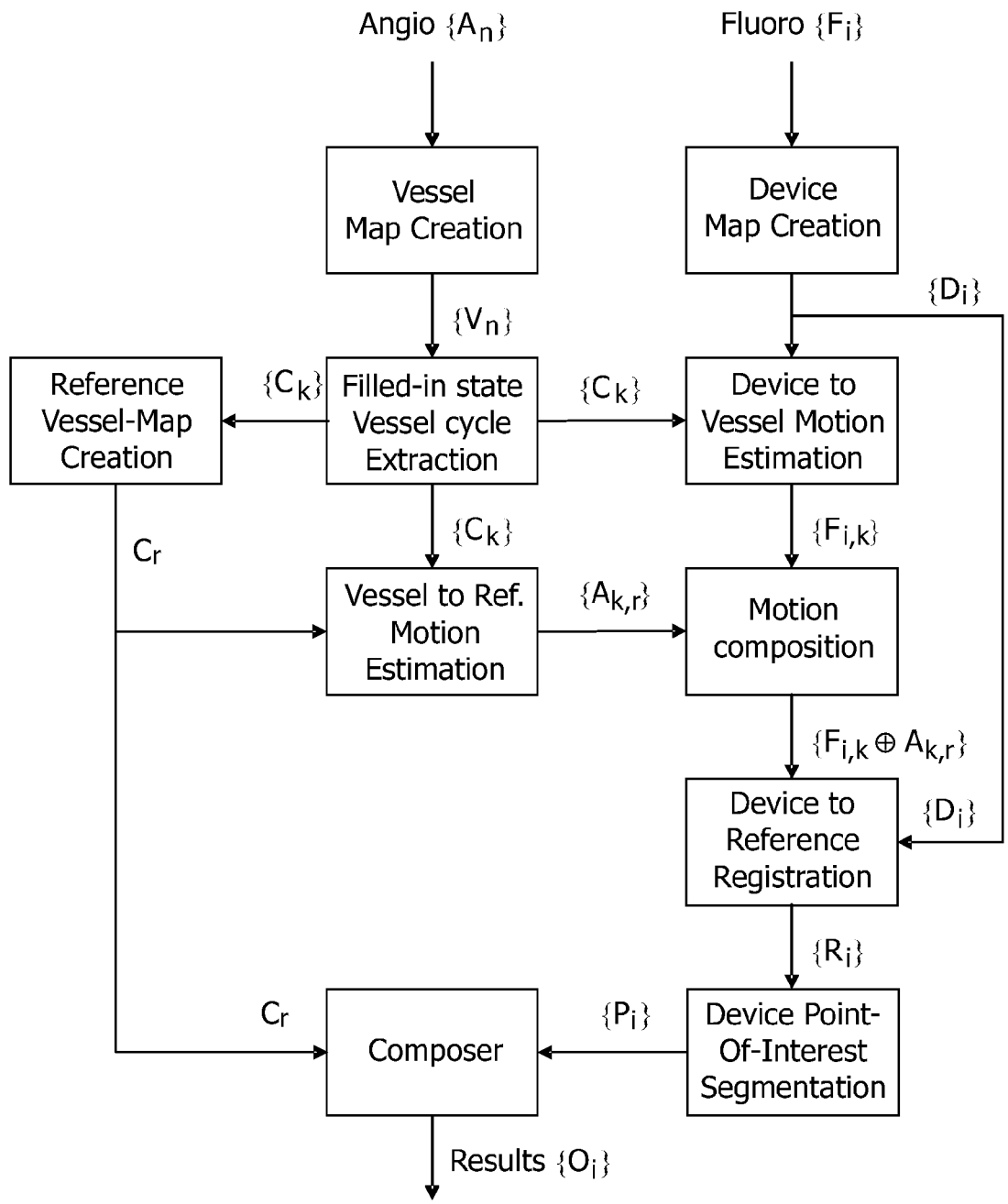
FIG. 2 shows a flow-chart of an exemplary embodiment of a method according to the present invention.

FIG. 2 shows a flow-chart of a method according to an exemplary embodiment of the present invention. The method depicted in FIG. 2 may be used for building a static cardiac roadmap for projecting an intervention object view onto this roadmap at the correct location.

In step 201 angiographic data $\{A_n\}$ are acquired. Furthermore, in step 202, fluoroscopic life-data $\{F_i\}$ are acquired.

The method relies on the construction of a vessel map (vessel map creation, step 203), which may simply be the result of a vessel segmentation or a map that provides, for each pixel, a likelihood of vessel presence. The vessel map is computed on the angiogram sequence $\{An\}$, and is itself a sequence of individual maps $\{Vn\}$ (one individual map per angiogram image).

Then, in step 205, a vessel cycle extraction is performed: Only a full cardiac cycle corresponding to vessels in the filled-in state (filled by contrast agent) may be needed. It may therefore be advantageous to extract such a cycle. One may rely on an electrocardiogram to perform such a task. This step may produce a subset $\{Ck\}$ of $\{Vn\}$ that corresponds to a filled-state full cardiac cycle.

Furthermore, in step 204, a device map is created (computed) on the fluoroscopy sequence $\{Fi\}$. Similarly to the vessel map, the device map may be a binary or Fuzzy segmentation of the intervention tools, i.e. an injection catheter, or a wire tip, or the like. Standard ridgeness filters and thresholding techniques may be used for this purpose. In any case, for each image of $\{Fi\}$ a device map is computed, thus producing a sequence $\{Di\}$.

In step 206, a device map to vessel map motion estimation is performed: Motion estimation between the device and the vessel maps can be applied after device map and vessel map creation. It may comprise finding the geometrical transformation (among a pre-defined class of possible transformations) that maximizes the similarity between the vessel maps $\{Ck\}$ and the device maps $\{Di\}$. Several similarity measurements might be considered.

This motion estimation step may take into account spatial-temporal constraints, and may be seen as a sequence-to-sequence motion estimation and matching operation (as opposed to an image-to-image or even to an image-to-sequence process). In addition to matching a device map Di to a vessel map Vk, this step may also compensate for the respiratory motions. Usually, the motion found is a global transform (capable of compensating for respiratory motion).

In any case, the output of the step is a sequence of vector fields $\{Fi,k\}$. Each vector field Fi,k is sufficient to bring into registration the device map Di to the vessel map Vk.

In step 207, a reference vessel map selection is performed: From the vessel map sequence $\{Ck\}$, a target static vessel map Cr, called the reference vessel map, is to be constructed. It may simply be one of the $\{Ck\}$, for instance the Ck showing a maximum visibility, or smallest distance to all others.

Then, in step 208, a vessel to reference motion estimation is performed: This step comprises the finding of motion vector fields in order to bring the vessel maps $\{Ck\}$ into registration with the reference vessel map Cr. Due to the complex nature of the cardiac motion, this may produce a sequence of elastic motion fields called $\{Ak,r\}$. Many elastic motion estimation techniques may be used for that purpose, for example optical flow.

In step 209, a motion composition is performed: The vector fields $\{Fi,k\}$ and $\{Ak,r\}$ are composed so as to obtain the sequence of motion vector fields $\{Fi,k \oplus Ak,r\}$ necessary to bring into registration the device maps $\{Di\}$ with the reference vessel map Cr. Standard motion composition techniques can be used, possibly involving vector interpolation steps.

In step 210, a device to reference registration is performed: The application of the composed motion vector fields $\{Fi,k \oplus Ak,r\}$ onto the device maps $\{Di\}$ produces a sequence of registered device maps called $\{Ri\}$.

In step 211, a device point-of-interest segmentation is performed: The point-of-interest of the intervention tools (usually the wire tip) that clearly represents the progress of the tool within the vasculature is to be extracted in the registered sequence $\{Ri\}$, thus producing a sequence $\{Pi\}$. Usual ridgeness techniques may be used to achieve this goal. However, the point-of-interest should have a sufficient signature for its unambiguous designation. This is usually the case with the guide-wire tip.

Apart from the tip, balloon markers are also typical point-of-interest objects that may be considered.

Figure 3:
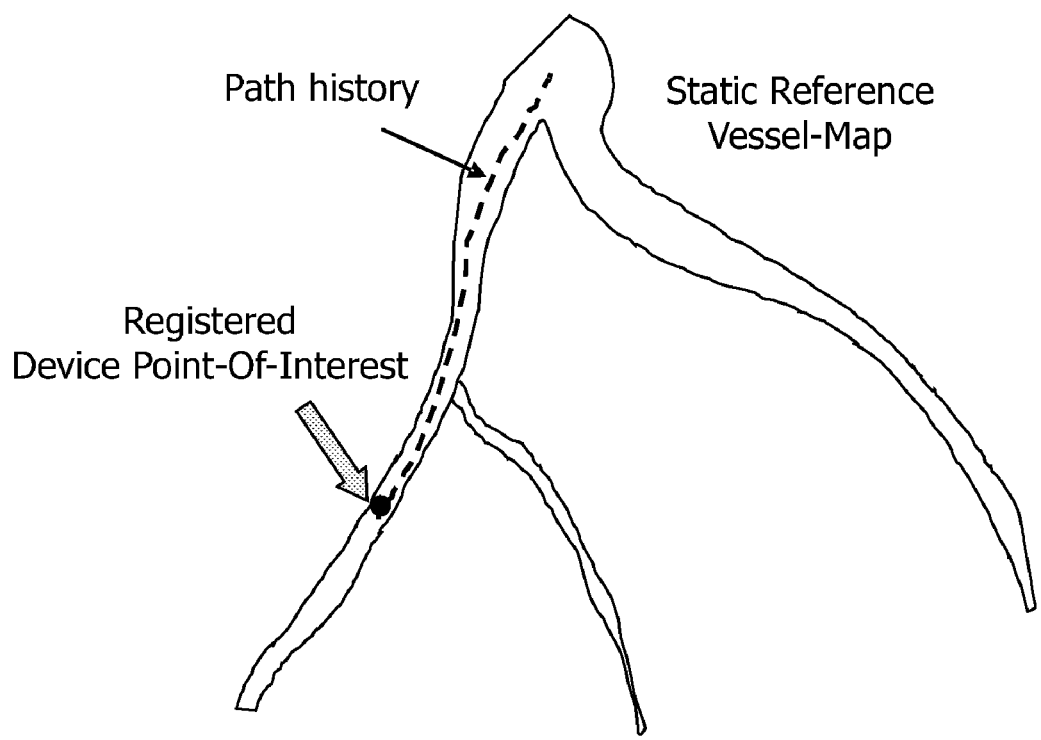
FIG. 3 shows a schematic representation of a composed image according to an exemplary embodiment of the present invention.

Step 212 is a composition or composer step, in which the sequence of the registered point-of-interests is superimposed to the reference vessel map, thus producing the final results, an example of which is depicted in FIG. 3. In addition, the composer may keep track of the recent point-of-interest path. All those features may be highlighted in various ways, i.e. by different colours, arrows, etc.

FIG. 3 shows a schematic representation of a vessel-tree 300 onto which the path of an interventional device 305 is projected. The interventional device 305 may be a guide-wire tip or a balloon marker. As may be seen from FIG. 3, the registered device point-of-interest has been moved along the path 304 before reaching the position 305. Path 304 lies within one specific arm 303 of the vessel-tree 300 (which further comprises arms 301, 302).

If necessary, the position of the tip 305 may be marked by a coloured arrow 306.

It should be noted, that several other embodiments may be provided. For example:

The exact sequencing described above may not be necessary in every case. For instance, the cycle extraction step may be skipped, in which case all the operations applied to {Ck} may be applied to {Vn}.

Furthermore, steps 210 and 211 (device to reference registration and device point-of-interest segmentation) may be swapped. One may apply the motion compensation directly to the point-of-interest segmentation result.

The computing of the motion fields may rely on the fact that, once registered, the point-of-interest should lie within the reference vessel-map. This may add constraints and may make the motion estimation more robust. It may also participate to the suppression of the device-to-roadmap jitter.

Several points-of-interest may be simultaneously considered and displayed on the reference vessel-map.

The reference vessel-map may also be replaced by a reference angiogram image when it comes to the final visualization.

Figure 4:
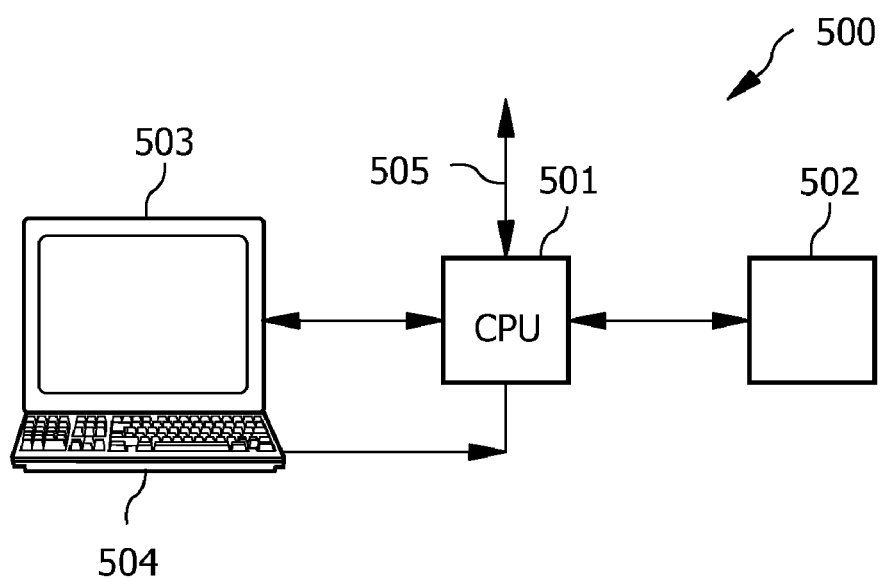
FIG. 4 shows an exemplary embodiment of an image processing device according to the present invention, for executing an exemplary embodiment of a method in accordance with the present invention.

FIG. 4 shows an exemplary embodiment of a data processing device 500 according to the present invention for executing an exemplary embodiment of a method in accordance with the present invention.

The data processing device 500 depicted in FIG. 4 comprises a central processing unit (CPU) or image processor 501 connected to a memory 502 for storing an image depicting an object of interest, such as the heart of a patient or an item of baggage. The central processing unit 502 may comprise a determination or calculation unit (not depicted in FIG. 5) according to an aspect of the present invention.

The data processor 501 may be connected to a plurality of input/output network or diagnosis devices, such as a computer tomography scanner. The data processor 501 may furthermore be connected to a display device 503, for example, a computer monitor, for displaying information or an image computed or adapted in the data processor 501. An operator or user may interact with the data processor 501 via a keyboard 504 and/or other input or output devices, which are not depicted in FIG. 4.

Furthermore, via the bus system 505, it may also be possible to connect the image processing and control processor 501 to, for example, a motion monitor, which monitors a motion of the object of interest. In case, for example, a lung of a patient is imaged, the motion sensor may be an exhalation sensor. In case the heart or a vessel-tree is imaged, the motion sensor may be an electrocardiogram.

Cardiac roadmapping according to the invention is perceived as a possible breakthrough since it may offer to the cardiologist an unprecedented way of achieving PTCA interventions with less contrast agent, less dose, less time, and more security.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

REFERENCES

[1] "Associating stored images with current images", K. Eck, G. Gijsbers, S. Mollus, WO 2004034329 A2, publication date 2 Dec. 2004.

[2] "Device and method for providing an angiographic image", K. Eck, J. Bredno, P. Rongen, WO 2005039253 A1, publication date 28 Apr. 2005.

[3] "Algorithmic Solutions for Live Device-to-Vessel Match". J. Bredno, B. Martin-Leung & K. Eck., In Proceedings of SPIE—Volume 5370—Medical Imaging 2004: Image Processing, J. Michael Fitzpatrick, Milan Sonka, Editors, May2004,pp. 1486-1497.

The invention claimed is:

1. A method for cardiac roadmapping for examination of an object of interest located in a volume of interest with an examination apparatus, the method comprising the steps of:
   creating an object of interest map sequence of the volume of interest on the basis of a first image sequence of the volume of interest;
   creating a device map sequence of the volume of interest on the basis of a second image sequence of the volume of interest;
   calculating a device map to object of interest map motion estimation to maximize the similarity between the device map sequence and the object of interest map sequence;
   creating a static reference map of the volume of interest on the basis of a first image sequence of the volume of interest, wherein the reference map is a static roadmap of the object of interest;
   calculating a reference motion estimation to bring the object of interest map sequence into registration with the static reference map;
   performing a motion composition to bring the device map sequence into registration with the static reference map, resulting in a navigation sequence; and
   displaying the navigation sequence as an image on a display device.

2. The method of claim 1,
   wherein the object of interest is a cardiac vessel-tree;
   wherein the first image sequence are angiograms of the object of interest;
   wherein the second image sequence is a life-time sequence acquired during an intervention of the object of interest; and
   wherein the reference map is a reference vessel-map.

3. The method of claim 1, wherein the motion composition is done by vector interpolation steps, resulting in a sequence of registered device maps.

4. The method of claim 1, wherein the static reference map of the volume of interest is selected by selecting the image of the first image sequence of the volume of interest having maximum visibility, or by selecting the image of the first image sequence of the volume of interest having smallest distance to all others.

5. The method of claim 1, wherein the object of interest map sequence of the volume of interest is subjected to a vessel cycle extraction corresponding to a full cardiac cycle.

6. The method of claim 1, wherein the device map to object of interest map motion estimation comprises a sequence-to-sequence motion estimation and matching operation.

7. The method of claim 1, further comprising a step of superimposing the sequence of registered device maps to the static reference map.

8. A non-transitory computer-readable medium comprising instructions for performing the steps of:
   creating an object of interest map sequence of the volume of interest on the basis of a first image sequence of the volume of interest;
   creating a device map sequence of the volume of interest on the basis of a second image sequence of the volume of interest;

calculating a device map to object of interest map motion estimation to maximize the similarity between the device map sequence and the object. of interest map sequence;

creating a static reference map of the volume of interest on the basis of a first image sequence of the volume of interest, wherein the reference map is a static roadmap of the Object of interest;

calculating a reference motion estimation to bring the object of interest map sequence into registration with the static reference map; and performing a motion composition to bring the device map sequence into registration. with the static reference map, resulting in a navigation sequence.

9. The computer-readable medium of claim 8,
wherein the object of interest is a cardiac vessel-tree;
wherein the first image sequence are angiograms of the object of interest;
wherein the second image sequence is a life-time sequence acquired during an intervention of the object of interest; and
wherein the reference map is a reference vessel-map.

10. The computer-readable medium of claim 8, wherein the motion composition is done by vector interpolation steps, resulting in a sequence of registered device maps.

11. The computer-readable medium of claim 8, wherein the static reference map of the volume of interest is selected by selecting the image of the first image sequence of the volume of interest having maximum visibility, or by selecting the image of the first image sequence of the volume of interest having smallest distance to all others.

12. The computer-readable medium of claim 8, wherein the object of interest map sequence of the volume of interest is subjected to a vessel cycle extraction corresponding to a full cardiac cycle.

13. The computer-readable medium of claim 8, wherein the device map to object of interest map motion estimation comprises a sequence-to-sequence motion estimation and matching operation.

14. The computer-readable medium of claim 8, further comprising a step of superimposing the sequence of registered device maps to the static reference map.

* * * * *